(12) United States Patent
Bowman et al.

(10) Patent No.: US 6,446,627 B1
(45) Date of Patent: Sep. 10, 2002

(54) INHALER DOSE COUNTER

(75) Inventors: Nicholas John Bowman, Royston; Michael John Holroyd, Great Shelford; Costaninos Panayi, Royston; William Richard Treneman, Oakington, all of (GB)

(73) Assignee: Norton Healthcare Limited, London (GB)

( * ) Notice: Subject to any disclaimer, the term of this patent is extended or adjusted under 35 U.S.C. 154(b) by 0 days.

(21) Appl. No.: 09/319,947

(22) PCT Filed: Dec. 18, 1997

(86) PCT No.: PCT/GB97/03480

§ 371 (c)(1),
(2), (4) Date: Oct. 22, 1999

(87) PCT Pub. No.: WO98/28033

PCT Pub. Date: Jul. 2, 1998

(30) Foreign Application Priority Data

Dec. 20, 1996 (GB) ............................................. 9626538

(51) Int. Cl.⁷ ............................................. A61M 11/00
(52) U.S. Cl. ............................. 128/200.23; 128/203.12
(58) Field of Search ....................... 128/200.14, 200.24, 128/203.12, 203.23

(56) References Cited

U.S. PATENT DOCUMENTS

| | | |
|---|---|---|
| 5,070,749 A | 12/1991 | Haviv |
| 5,437,270 A | 8/1995 | Braithwaite |
| 5,482,030 A | 1/1996 | Klein |
| 5,655,523 A * | 8/1997 | Hodson et al. ......... 128/203.12 |
| 5,740,793 A * | 4/1998 | Hodson et al. ......... 128/203.15 |
| 6,012,454 A * | 1/2000 | Hodson et al. ......... 128/203.15 |

FOREIGN PATENT DOCUMENTS

| | | |
|---|---|---|
| EP | 0 254 391 | 1/1988 |
| EP | 0 296 496 | 6/1988 |
| EP | 0 480 488 | 4/1992 |
| GB | 1 216 626 | 12/1970 |
| GB | 1 554 272 | 10/1979 |
| GB | 2 191 032 | 12/1987 |
| GB | 2 282 267 | 3/1995 |
| WO | 86 02775 | 4/1986 |
| WO | 92 09324 | 6/1992 |

* cited by examiner

Primary Examiner—Glenn K. Dawson
(74) Attorney, Agent, or Firm—Arent Fox Kintner Plotkin & Kahn, PLLC

(57) ABSTRACT

A dose counter for a metered dose inhaler comprises actuator means (341), drive means (350) for driving a rotary gear (360) in step-wise fashion in response to displacement of said actuator means (341), said rotary gear (360) comprising a wheel having a plurality of ratchet teeth (not shown) around its periphery. Means (364) are provided to prevent reverse rotation of the rotary gear (360). A flexible tape (368) is provided with a visible array of incrementing integers on its surface indicating the number of medicament doses remaining in the inhaler. The tape (368) indexes by a single integer in response to each step of the step-wise rotary motion of the rotary gear (360). A control surface (371) regulates the position of engagement and disengagement between the drive means (350) and the rotary gear (360). In an alternative embodiment (FIG. 6), the control surface (371) is omitted and the means for preventing reverse rotation comprise a stepless restraint (664).

33 Claims, 7 Drawing Sheets

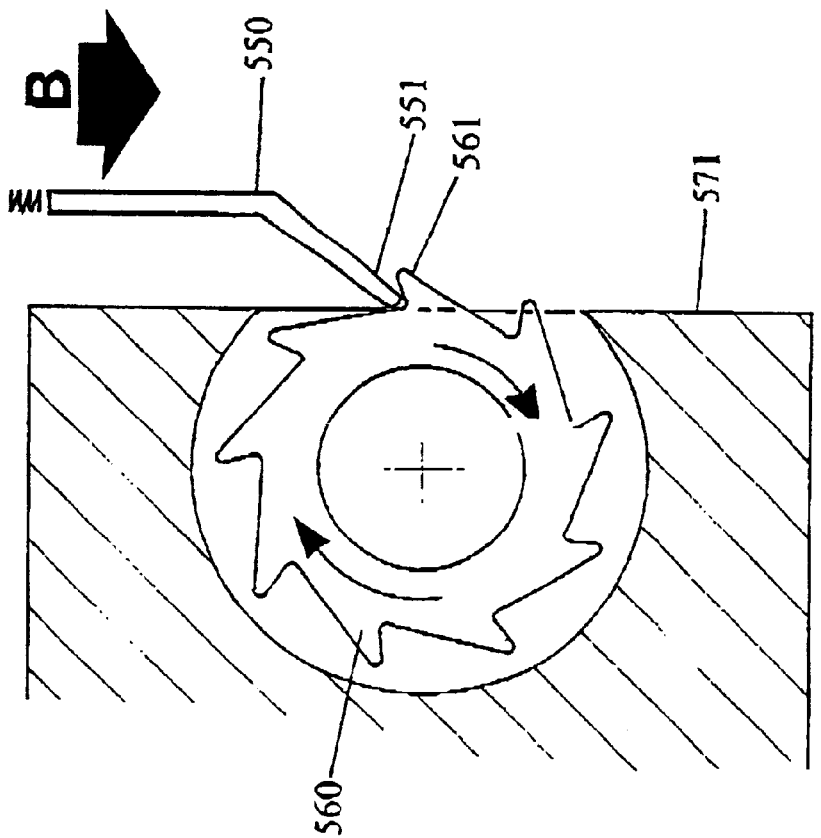
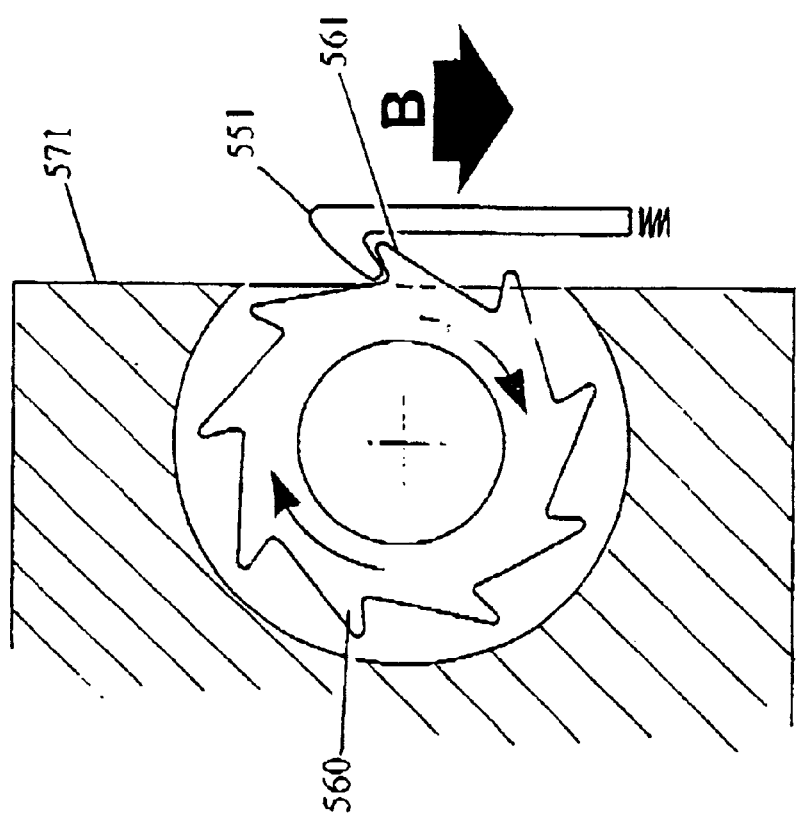
Figure 5

INHALER DOSE COUNTER

The present invention relates to a dose counter for a portable dispensing device of the type used for dispensing discrete amounts of a fluid or particulate material entrained in an air or other propellant stream. In particular, the invention is concerned with dose counters for portable dispensing devices of the metered dose inhaler type which are well known in the art of medicine for treatment of, or alleviation of the effects of, respiratory complaints such as asthma.

Metered dose inhalers typically consist of a medicament-containing vessel and an actuator body having a drug delivery outlet. The present invention will find utility in any type of metered dose inhaler in which the contents of the medicament reservoir are invisible to the user, including pressurised metered dose inhalers (of both manually-operable and breath-actuated types), dry powder inhalers, or such like.

The medicament-containing vessel may be a pressurised canister containing a mixture of active drug and propellant. Such canisters are usually formed from a deep drawn aluminium cup portion having a crimped lid portion which carries a metering valve assembly. The metering valve assembly is provided with a protruding valve stem which, in use, is inserted as a tight push fit into a so-called "stem block" in the actuator body.

To actuate the conventional manually-operable inhaler, the user applies a compressive force to the closed end of the canister. The internal components of the metering valve assembly are spring loaded so that, typically, a compressive force of between 15 and 30 N is required to activate the device. In response to this compressive force, the canister moves axially with respect to the valve stem by an amount varying between about 2 and 4 mm. This degree of axial movement is sufficient to actuate the metering valve and cause a metered quantity of the drug and propellant to be expelled through the valve stem. This is then released into the mouthpiece via a nozzle in the stem block. A user inhaling through the drug delivery outlet of the device at this point will thus receive a dose of the drug.

Metered dose inhalers as described above administer an accurate dose of medicament whenever required, which is particularly useful for users whose respiratory difficulties manifest themselves suddenly. Such has been the success of these devices that they are now used throughout the world, where they are exposed to a wide variety of climatic conditions.

A more recent development is the so-called "breath-operated actuator" which delivers a dose of drug through a mouthpiece in response to inhalation by the user. This type of arrangement is particularly convenient in circumstances where the co-ordination between user inhalation and manual depression of the aerosol canister is imperfect. For example, children sometimes lack the necessary co-ordination to achieve effective self-administration. At times of respiratory distress, adult users may also experience poor co-ordination.

Unfortunately, one of the drawbacks of self-administration from an inhaler is that users often experience difficulty in determining when the charge in the medicament-containing vessel has nearly run out. With aerosol canisters, part of the reason for this difficulty is that a surplus of propellant may remain in the canister even though the drug supply is nearly used up. Alternatively, the near-exhausted state may result in a surplus of drug in relation to propellant. Thus, the illusion is created that the inhaler is still capable of providing useful doses of medicament simply because the canister contains liquid. This is potentially hazardous for the user since dosing becomes unreliable and because few people routinely carry a back-up device.

Many users have several different inhalers for the treatment of a variety of conditions. Others keep inhalers at a number of different locations such as at school, home, work etc. In these circumstances it is particularly difficult for the user to keep track of the amount of usage extracted from each individual inhaler apparatus.

Clearly there is a need for a counter mechanism which enables users to assess how many doses remain in the obscured canister. Such a counter would ensure that users are warned when the inhaler nears exhaustion so that appropriate measures can be taken to avoid running out of medication. Moreover, if a dose counter can provide readability to a resolution of one dose, this can be used for compliance monitoring, either under hospital supervision or by parents and teachers assessing compliance by children in their care.

To this end, various counters have been proposed in recent times which aid the management of metered dosage. Such counters vary in complexity and sophistication, but they all have in common the feature that they detect relative movement between the medicament-containing vessel and the actuator body and increment in response to such movement.

Known dose counters can be categorised into the following types:
 (a) Reservoir low indicators,
 (b) Fuel gauge types (resolution limited to 10 doses or higher),
 (c) Dose computers (resolution to one dose and intrinsically accurate).

An example of the first type is described in International Patent Application No. WO 86/05991 which uses a wheel carrying a coloured mark as the warning indicator. The wheel is rotated by a worm drive forming part of the metering mechanism. Actuation of the metering mechanism infers that the patient has taken a dose of medicament and, when a predetermined number of doses has been dispensed, the coloured part of the wheel becomes visible through an aperture. This indicates to the user that a replacement dispenser will be required shortly. The principles disclosed in this document would enable the system to be upgraded to a fuel gauge type display except for the fact that the worm gearing system is unsuitable for providing single dose resolution in a portable product.

International Patent Application No. WO 92/09324 discloses the use of a rotatable display means incorporating a rack of teeth which is driven by a ratchet during the dispensing of a medicament dose. Each tooth on the rack corresponds to a single dose. The disadvantage of this type of arrangement is that, for reliable operation, all of the teeth in the rack need to be perfect. One poor tooth will result in the counter display showing "half full" when the reservoir is actually empty. The document also discloses a number of gearing means to enable the display to increment for hundreds of doses. To provide a counter for the typical 200-dose portable inhaler using this invention would require a wheel with very small teeth, formation of which is beyond current manufacturing capabilities at sensible costs.

European Patent Application No. 0 480 488 discloses a similar dose counter using a rack of single-direction teeth as the recording means. This arrangement typifies the current state of the art and its inherent limitations. The display ring shows the doses remaining, but only in units of ten.

Furthermore, for reasons of tooth size, the display ring limits the reservoir capacity to a total of approximately counted 120 doses. By means of further reduction in gearing it is possible for this type of system to be extended to 200 doses but only by reducing the display resolution to greater than 10 doses.

U.S. Pat. No. 4,565,302 discloses similar means to the devices discussed above, but illustrated clearly in FIG. 6 the limitations of such mechanisms in terms of display readability and total reservoir size. To ensure readability, a large numeral 5 is shown in the device; it is clear from the Figure that no more than 30 doses could be displayed in this manner if the same style and size of indication is required for each dose dispensed i.e. 5, 4, 3 etc.

In U.S. Pat. No. 5,437,270 for a multi-dose powder device, a number of display means are disclosed, including a tape system. The system is described as a tape wound up into a roll and which is freely rotatable, the leading edge of the tape being secured to a drum coupled to the rotation of the metering member. The metering member is described as being rotated through a known angular increment by a ratchet system linked to a linear button that the patient presses to meter a dose.

An example of a dose computer is described in International Patent Application No. WO 91/06334. This document discloses an electronic method of counting doses remaining in the medicament canister using a switch triggered by the can movement: the switch actuation is recorded by a microprocessor which displays the remaining doses on a screen. This system was invented for monitoring clinical studies and includes date/time logging and means for data downloading. This was the first patent to show an implementation of a true electronic dose computer.

Numerous other patent applications have followed, disclosing other dose sensing means (usually inferred from the movement of the metering valve) coupled to electronic means of recording the doses.

One of the drawbacks of these known counters is that they rely on mechanical interaction between parts attached to the medicament-containing vessel and parts provided on the actuator body. In other words, they are displacement-triggered. Such counters are difficult to manufacture with satisfactory tolerances because of the variation in length of typical aerosol canisters which is attributable in part to the crimping operation used to connect the valve-carrying lid portion to the main cup portion. Another variable is the length of stroke of the metering valve. Although the technology involved is not especially demanding, it has been found that the amount of travel effective to actuate the metering valve of a typical medicament-containing aerosol canister may fall in a tolerance band as small as 0.5 mm. Thus it is difficult to provide a generic counter which increments accurately in response to every actuation. This may be true even when the counter, the aerosol canister and the inhaler housing have been specifically designed for use together. The problem is therefore likely to be worse in circumstances where different manufacturers' aerosol canisters, inhaler housings and displacement-triggered counters are used in combination.

International Patent Application No. WO 96/00595 discloses the use of a heat sensor which detects the heat of evaporation of the propellant and thus truly detects the delivered dose. However, this device suffers from the common drawback of all electronic dose counters in that it is relatively expensive.

It is therefore an object of the present invention to combine the following advantages in a mechanical counter:

(1) Absolute intrinsic reliability in use—an unreliable counter is worse than no counter at all.
(2) Single dose readability over 200 doses or more.
(3) Low cost to suit disposable products.
(4) Small size with large display to suit portable inhalers.

In a first aspect, the invention is a dose counter for a metered dose inhaler, the counter comprising:

actuator means;

drive means for driving rotary gear means in step-wise fashion in response to displacement of said actuator means, said rotary gear means comprising a wheel mounted on a spindle and said wheel having a plurality of ratchet teeth around its periphery;

means to prevent reverse rotation of said rotary gear means;

display means coupled to the rotary motion of said rotary gear means, said display means having a visible array of incrementing integers on a surface thereof indexable by a single integer in response to each step of the step-wise rotary motion of the rotary gear means;

characterised in that said dose counter further comprises a control surface to regulate the position of engagement and disengagement between said drive means and said wheel.

Preferably, the actuator means are operable by linear displacement from a first position to a second position and back to said first position and the count index occurs during the forward stroke of the actuator means from said first position to said second position. For example, the actuator means may comprise a spring-loaded plunger adapted to engage the rim of a medicament reservoir and being depressible against the return force of the spring loading when the medicament reservoir is translated to deliver a dose of medicament through its metering valve. The actuator means may be integrally formed with the drive means.

By controlling the position of engagement and disengagement between the drive means and the wheel, the travel required to count is precisely regulated. For maximum reliability and accuracy, the counter must only index after the metering valve has delivered its dose from the inhaler. If it counts before this, users can index the counter without receiving a dose of medicament. In extreme cases, the user could end up with a counter reading empty when the medicament reservoir is actually full. Hence, the travel from rest to the fire point can be defined as the "must not count" zone.

As soon as possible after firing, the counter needs to index, the upper limit being the extent of full travel of the metering valve. This can be defined as the "must count" zone. Since all assemblies have tolerances necessary for reliable production, part of the "must count" zone is required for the fire position variance and part for the full valve travel variance.

Although typical valve travels are between 3 and 5 mm, only part of this travel is available to index a counter mechanism. Hence the actual requirement for a counter is that it must index after 2 mm of travel and be capable of accepting 5 mm of travel without double counting.

IN known ratchet indexing mechanisms, a drive element is used to engage a one-direction tooth form of a rack. The rack may be linear or it may be turned upon itself to form a toothed wheel. The drive element engages in the first rack tooth and moves the whole rack a distance greater than one tooth pitch. The rack must then remain in the new position while the drive element disengages from the first tooth and engages the next. The temporary holding of the rack is commonly achieved by a fixed element or pawl that engages a tooth form on the rack and prevents reverse motion.

In order that only one tooth is indexed for each drive element movement, the rack travel must exceed one tooth pitch but be less then two tooth pitches. Thus, the chosen pitch must match the available travel, with nominal travel being set typically at 1.5 tooth pitches. The maximum range of travel is therefore between one and two tooth pitches.

Unfortunately the tolerances encountered in metering valves for inhaler devices fall outside this band. If the "must count" zone begins at 2 mm of travel and extends to between 3 and 5 mm, it is impossible to determine a tooth pitch when is universally applicable to all inhaler variants.

The control surface overcomes this problem by regulating the point of engagement as well as the point of disengagement between the toothed wheel and the drive element. It then becomes possible to use a small circular rack to obtain precise increments. By extending the control surface beyond the circular rack in both directions, it is possible to provide a precise rotational increment from linear valve travel even when the linear motion far exceeds that required for the rotational increment. Using this invention, the maximum precision of incrementation is obtained without the possibility of double counting or sensitivity to variation in linear travel.

In an especially preferred variant, the means to prevent reverse rotation of the rotary gear means is a friction clutch such as a wrap-spring clutch. The advantage of a wrap-spring clutch is that it operates on the spindle mounting the ratchet wheel and braces the spindle against reverse rotation relative to the counter chassis. Absence of side forces acting on the ratchet wheel means that mechanical operation of the counter is simplified.

Advantageously, the drive means for driving the rotary gear means comprises a ratchet drive pawl in the form of a straddle drive in which the element that engages the ratchet teeth of the wheel is supported between a pair of spaced apart support arms. The gap between the support arms is dimensioned to accommodate the thickness of the wheel therebetween, so that the depth of engagement between the ratchet drive pawl and the ratchet teeth of the wheel is unhindered by the drive means support.

Preferably, the display means is an elongate flexible web such as a paper or plastics tape on which the dose amount is printed, say as a descending sequence of numbers from e.g. 200. The advantage of a tape display is that different print styles or representations can be easily incorporated to emphasise significant events to the inhaler user, such as approaching exhaustion of the medicament reservoir. The tape is dispensed from a supply spool which is arranged in parallel with a take-up spool. The take-up spool may share the same spindle as that on which the ratchet wheel is mounted. The tape extends between the two spools and passes behind a window in the inhaler apparatus through which one of the printed figures is visible to the user.

In a second aspect, the invention is a dose counter for a metered dose inhaler, the counter comprising:
  actuator means;
  drive means for driving rotary gear means in step-wise fashion in response to displacement of said actuator means, said rotary gear means comprising a wheel mounted on a spindle and said wheel having a plurality of ratchet teeth around its periphery;
  display means coupled to the rotary motion of said rotary gear means, said display means having a visible array of incrementing integers on a surface thereof indexable by a single integer in response to each step of the step-wise rotary motion of the rotary gear means;
  characterised in that said dose counter further comprises stepless restraint means to prevent reverse rotation of said rotary gear means.

Preferably, the stepless restraint means is a wrap-spring clutch operating on the spindle on which the ratchet wheel is mounted and bracing the spindle against reverse rotation relative to the counter chassis. Absence of side forces acting on the ratchet wheel means that mechanical operation of the counter is simplified.

The actuator means may be operable by linear displacement from a first position to a second position and back to said first position, the count index occurring during the forward stroke of the actuator means from said first position to said second position. For example, the actuator means may comprise a spring-loaded plunger adapted to engage the rim of a medicament reservoir and being depressible against the return force of the spring loading when the medicament reservoir is translated to deliver a dose of medicament through its metering valve. The actuator means may be integrally formed with the drive means.

The drive means for driving the rotary gear means may be a ratchet drive pawl in the form of a straddle drive in which the element that engages the ratchet teeth of the wheel is supported between a pair of spaced apart support arms. The gap between the support arms is preferably dimensioned to accommodate the thickness of the wheel therebetween, so that the depth of engagement between the ratchet drive pawl and the ratchet teeth of the wheel is unhindered by the drive means support.

Preferably, the display means is an elongate flexible web of paper or plastics material on which the dose count is printed, for example as a descending sequence of numbers from e.g. 200. The advantage of a tape display is that different print styles or representations can be easily incorporated to emphasise significant events to the inhaler user, such as approaching exhaustion of the medicament reservoir. The tape is dispensed from a supply stool which is arranged in parallel with a take-up spool. The take-up spool may share the same spindle as that on which the ratchet wheel is mounted. The tape extends between the two spools and passes behind a window in the inhaler apparatus through which one of the printed figures is visible to the user.

In a third aspect, the invention is a dose counter for a metered dose inhaler, the counter comprising:
  actuator means;
  drive means for driving rotary gear means in step-wise fashion in response to displacement of said actuator means, said rotary gear means comprising a wheel mounted on a spindle and said wheel having a plurality of ratchet teeth around its periphery;
  display means coupled to the rotary motion of said rotary gear means, said display means having a visible array of incrementing integers on a surface thereof indexable by a single integer in response to each step of the step-wise rotary motion of the rotary gear means;
  characterised in that said dose counter further comprises a ratchet and drive pawl mechanism including a rack having an array of ratchet teeth and drive pawl means in the form of a straddle drive in which the element that engages the ratchet teeth is supported between a pair of spaced apart support arms.

The gap between the support arms is preferably dimensioned to accommodate the thickness of the rack therebetween, so that the depth of engagement between the ratchet drive pawl and the teeth of the rack is unhindered by the drive means support. This arrangement helps to equalise the forces on either side of the tooth-engaging element and minimises twisting. The drive pawl may be used either to pull the ratchet teeth or to push them.

The invention will now be described by way of example only with reference to the drawings, in which.

Figures 6A, 6B:
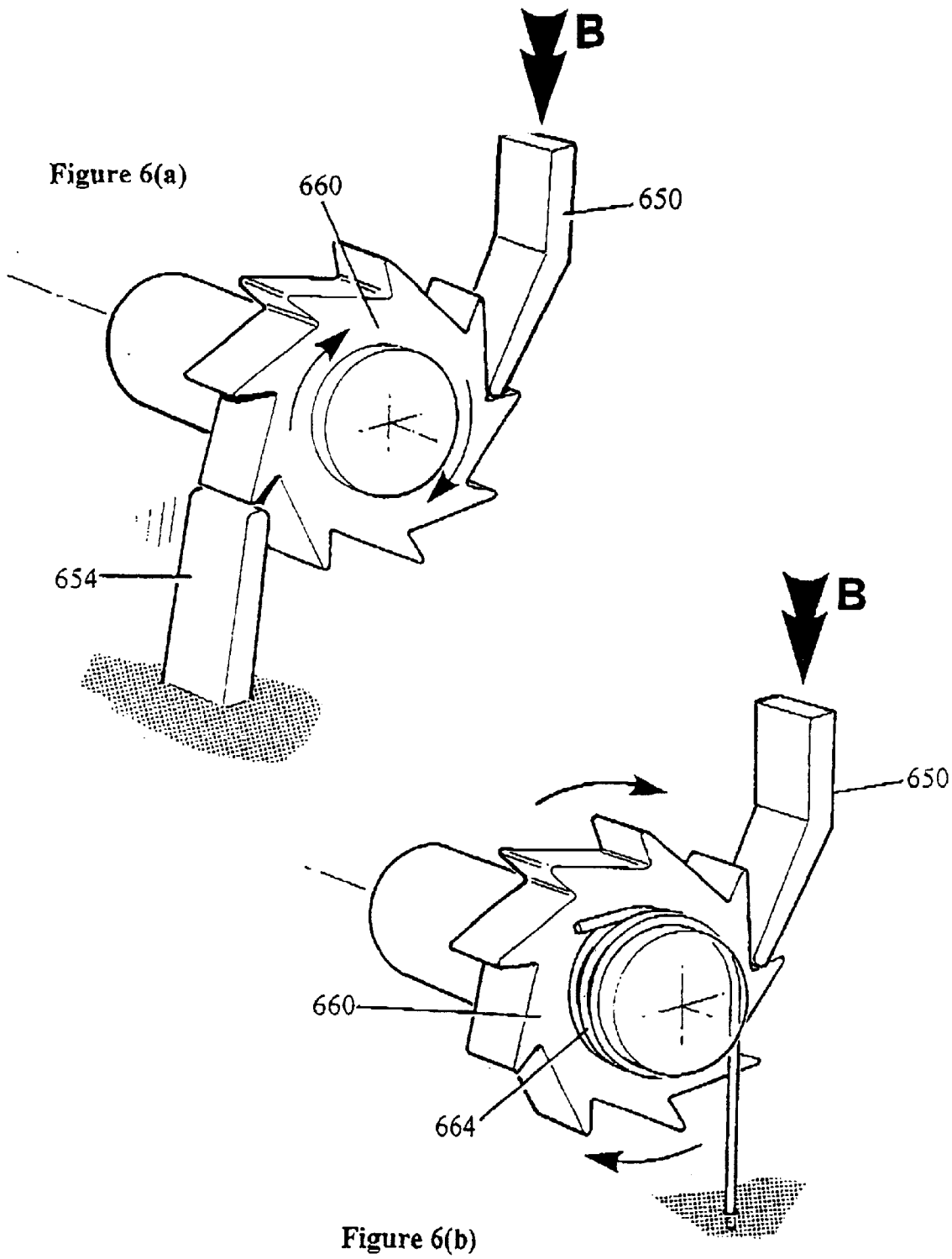
Figure 7:
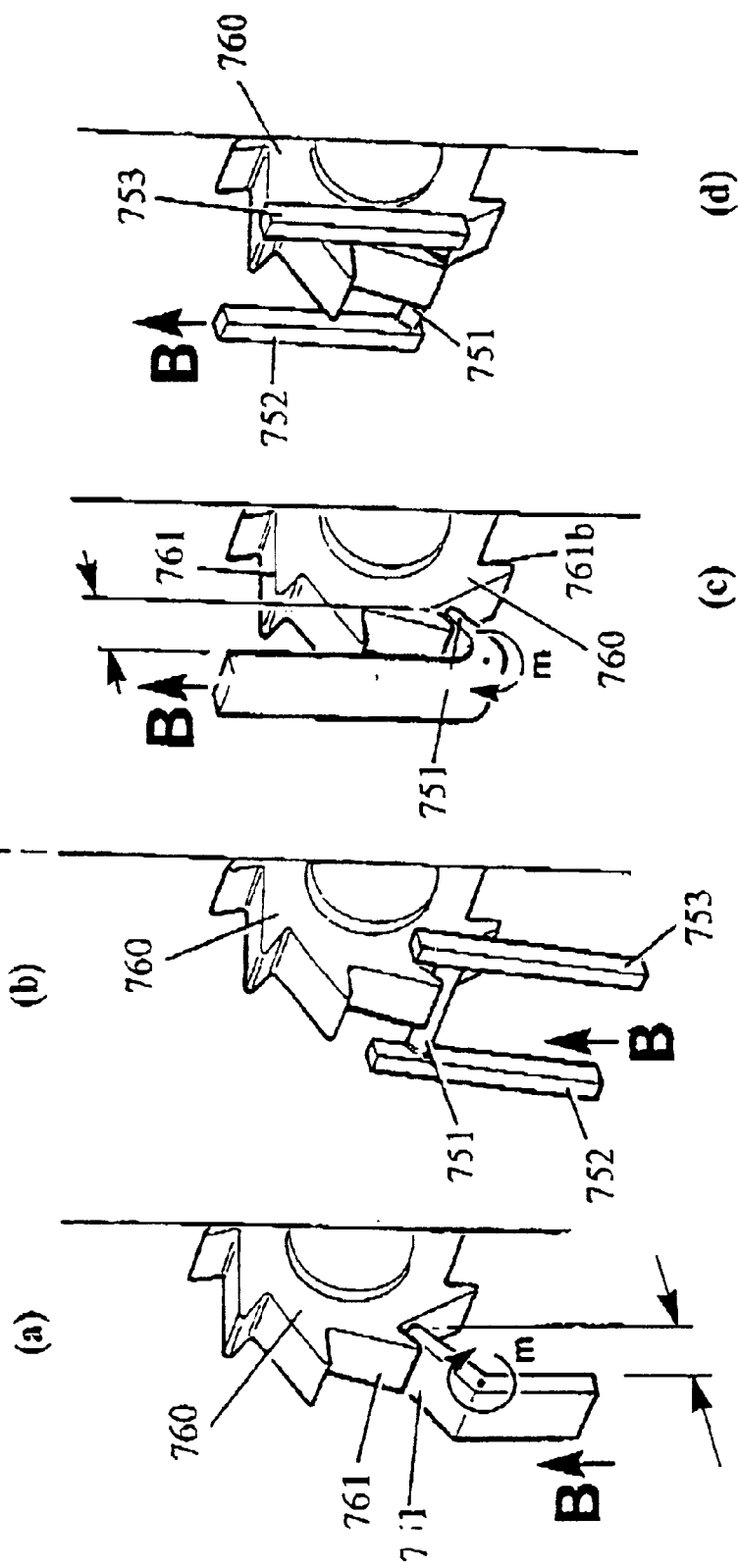

FIG. 5, views (a) and (b) show schematically two possible arrangements of ratchet gear and drive pawl in accordance with a first aspect of the invention;

FIG. 6, views (a) and (b) show schematically a stepped restraint and a stepless restraint acting on a ratchet gear and drive pawl arrangement, and FIG. 7 [views (a)–(d) are] a series of schematic views comparing conventional ratchet drives with straddle drives in accordance with a third aspect of the invention.

Figure 1:
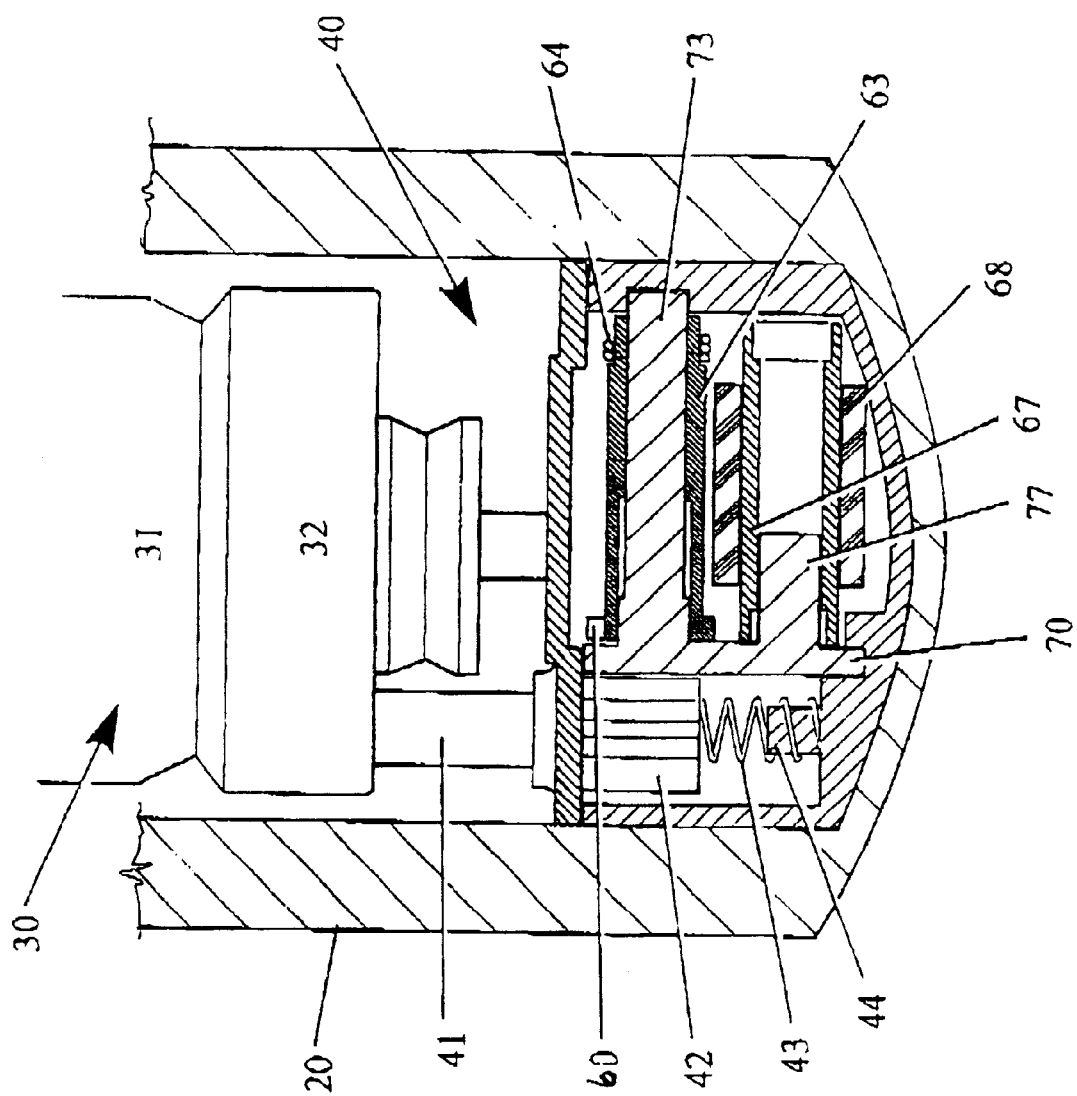
FIG. 1 is a cross-sectional view through an inhaler apparatus showing a counter mechanism in accordance with the present invention in position near the base of an inhaler actuator.
Figure 2:
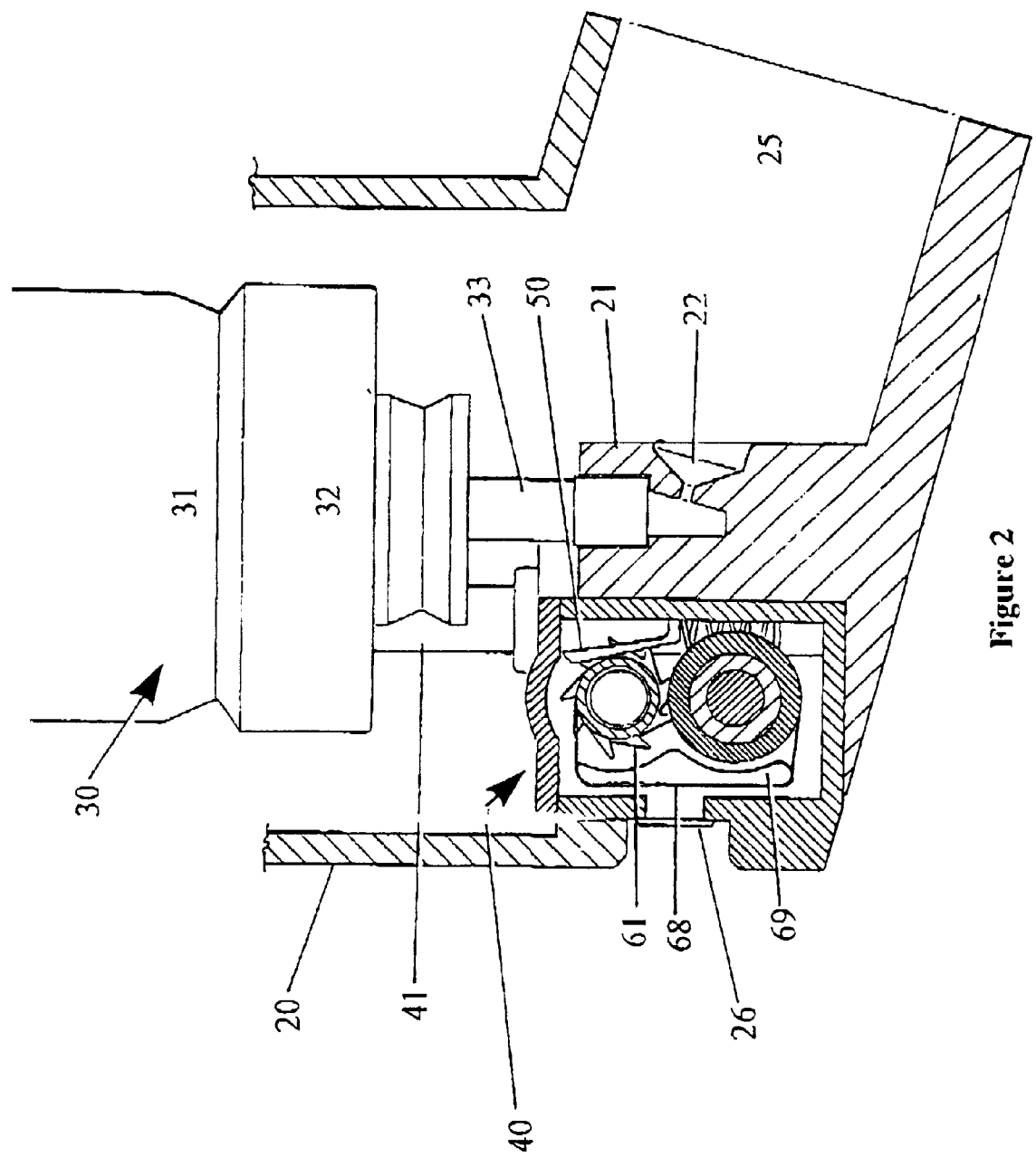
FIG. 2 is a cross-sectional view taken at right angles to the view of FIG. 1.

Referring now to FIGS. 1 and 2, the lower portion of a metered dose inhaler is shown, comprising an actuator body 20 having a drug delivery outlet 25. An aerosol canister 30 extends into the lower portion of the actuator body 20. The aerosol canister 30 is formed from a deep drawn aluminium cup section 31 to which a lid portion 32 is attached by crimping. The lid portion 32 carries a metering valve assembly having a protruding valve stem 33, the end of which is received as a tight push fit in a stem block 21 of the actuator body 20. Stem block 21 has a nozzle 22 communicating with the drug delivery outlet 25 so that, upon actuation of the metering valve assembly, a charge of the drug is emitted through the nozzle 22 into the drug delivery outlet 25. Actuation of the metering valve assembly is effected by causing downward movement of the aerosol canister 30 relative to the actuator body 20. This may be achieved through manual pressure exerted by the user against the upturned base (not shown) of the aerosol canister 30 or by automatic depression of the aerosol canister 30 in response to user inhalation in inhalers of the breath-actuated type. The mechanism of breath actuation does not form part of the present invention and will not be described in greater detail in this specification. A user inhaling through the drug delivery outlet 25 when the aerosol canister 30 is depressed will receive a metered dose of the drug.

A counter mechanism generally designated by the reference numeral 40 includes an actuator plunger 41 moulded from a plastics material such as nylon, the plunger 41 having a boss portion 42 integrally formed at its base. The underside of boss portion 42 is formed with a blind hole which receives a compression spring 43 mounted on an upstanding spigot 44 formed on a lower element of the counter chassis.

Drive means 50, for driving a rotary gear means in the form of a ratchet-toothed wheel 60, is integrally moulded with boss portion 42 of the actuator and comprises a transverse hook element (not shown) mounted between two arms 52, 53 (only one visible in FIG. 2), the bases of which are conjoined to the boss portion 42. The transverse hook element is dimensioned and oriented to engage with ratchet teeth 61 formed around the periphery of ratchet wheel 60 to rotate it in a forward direction.

Ratchet wheel 60 is integrally moulded with a first hollow axle 63 which is rotatably supported on a first spindle 73 that projects transversely from a chassis sub-element 70. Chassis sub-element 70 also has a second spindle 77 projecting transversely therefrom on which a second hollow axle 67 is rotatably supported. A flexible tape 68 is wound around the second hollow axle 67 which serves as a supply spool and passes to the first hollow axle 63 which serves as a take-up spool. A guide plate 69 forming part of the chassis sub-element 70 helps to guide the tape in a smooth passage from the supply spool to the take-up spool. The surface of the tape 68 is marked with a progression of descending numbers which denote the number of doses remaining in the aerosol canister. Typically, the starting count is 200 and successive markings on the tape decrease by one. The spacing between successive markings is coincident with the indexing motion of the matching wheel 60 so that a new number appears in a window 26 provided in the inhaler housing 20 for each successive actuation.

The ratchet-toothed wheel 60 and integrally formed first hollow axle 63 are restrained from reverse rotation by a wrap-spring clutch 64 surrounding the hollow axle 63 at the end thereof remote from ratchet-toothed wheel 60. One end (not shown) of the wrap-spring clutch 64 is braced against the counter chassis. The windings of the wrap-spring clutch 64 are oriented such that rotation of the first hollow axle 63 in a forward sense is not resisted by the spring coils. However, reverse rotation of the hollow axle 63 acts so as to tighten the spring coils around it, thereby causing the first hollow axle 63 to be gripped by the internal surface of the wrap-spring clutch 64 and hence restraint from reverse rotation.

Figure 3:
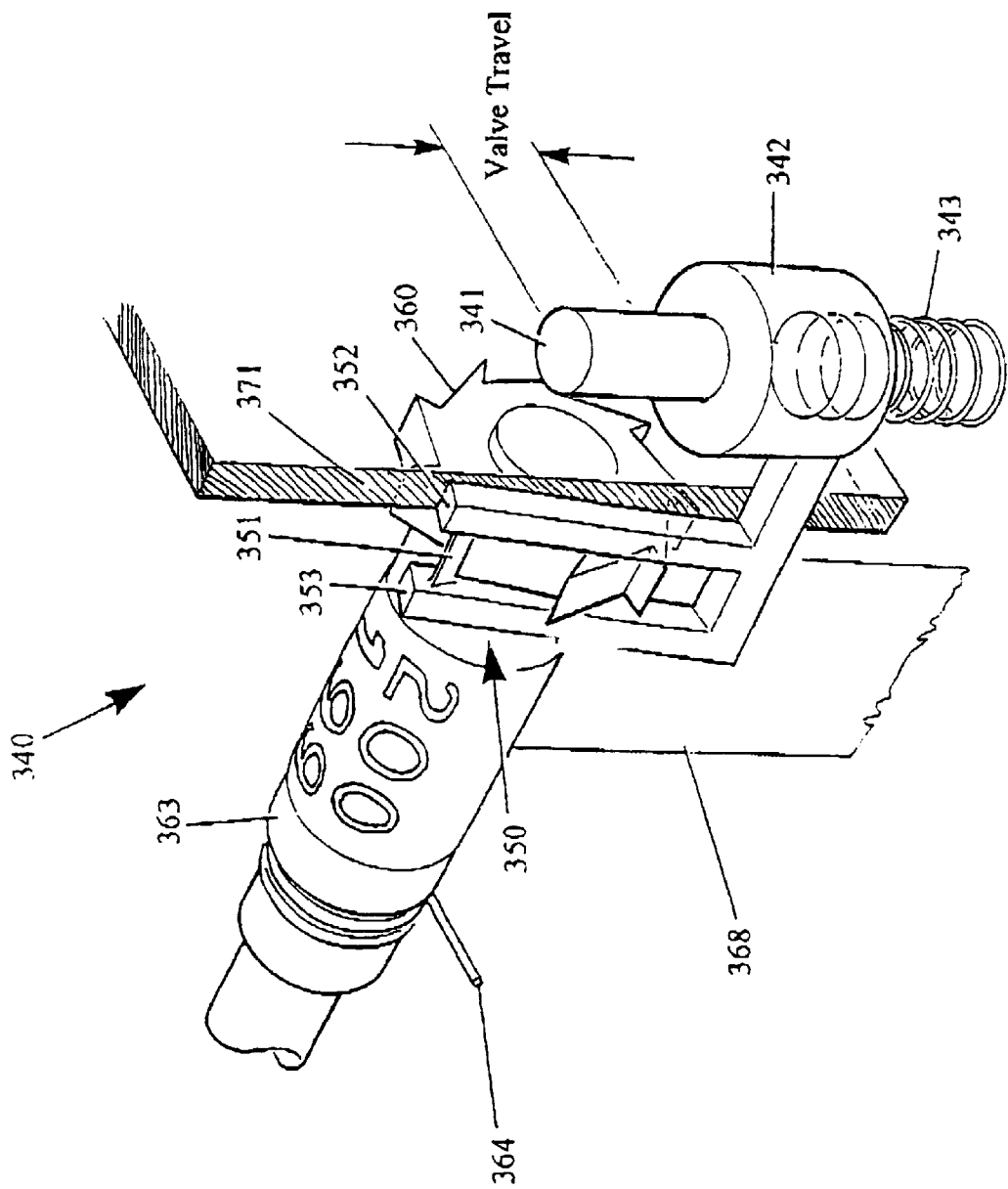
FIG. 3 is a schematic perspective view of an especially preferred form of the invention from which unessential detail of the inhaler housing has been omitted for clarity.

Turning now to FIG. 3, this drawing depicts a preferred embodiment of the invention in schematic perspective view. The counter mechanism is generally designated by the reference numeral 340 and consists of an actuator 341 having a boss portion 342 integrally formed therewith and drive means 350 joined to the boss portion 342. The underside of boss portion 342 is provided with a blind hole which receives a compression spring 343 that serves to return the actuator 341 to its rest position after depression thereof during actuation of the inhaler apparatus (not shown).

The drive means 350 comprises a transverse hook element 351 mounted between a pair of arms 352, 353 which are joined at their bases by a web. The web is connected to the boss portion 342 of the actuator 341 and a combined actuator and drive means assembly may be integrally formed from a plastics material such as nylon.

In use, the transverse hook element 351 engages with ratchet teeth of a ratchet-toothed wheel 360 which is mounted on a hollow axle 363 serving as a take-up spool for a flexible tape display 368. At the end of the hollow axle 363 remote from the ratchet-toothed wheel 360 is a friction clutch 364 which serves to restrain the axle 363 against reverse rotation and hence prevents reverse travel of the counter tape 368.

Also shown in this view is a control surface 371 which is depicted here as a see-through element so that the workings of the invention may be more clearly understood. Control surface 371 extends parallel to the direction of travel of the actuator 341 and is located adjacent the ratchet-toothed wheel 360 at a position which marks a chordal projection across one of the wheel faces. One of the support arms 352 of the drive means 350 is in sliding contact with control surface 371. This sliding contact serves to inhibit the natural tendency of the drive means 350 to flex radially inwardly towards the axis of rotation of the ratchet-toothed wheel 360. By preventing such radially inward flexure, the control surface 371 restricts the engagement and disengagement of the drive 350 with the ratchet-toothed wheel 360 so that the distance by which the ratchet-toothed wheel 360 rotates is limited to one tooth pitch. This condition is observed regardless of the extent of linear travel, or stroke, of the actuator 341.

Figure 4:
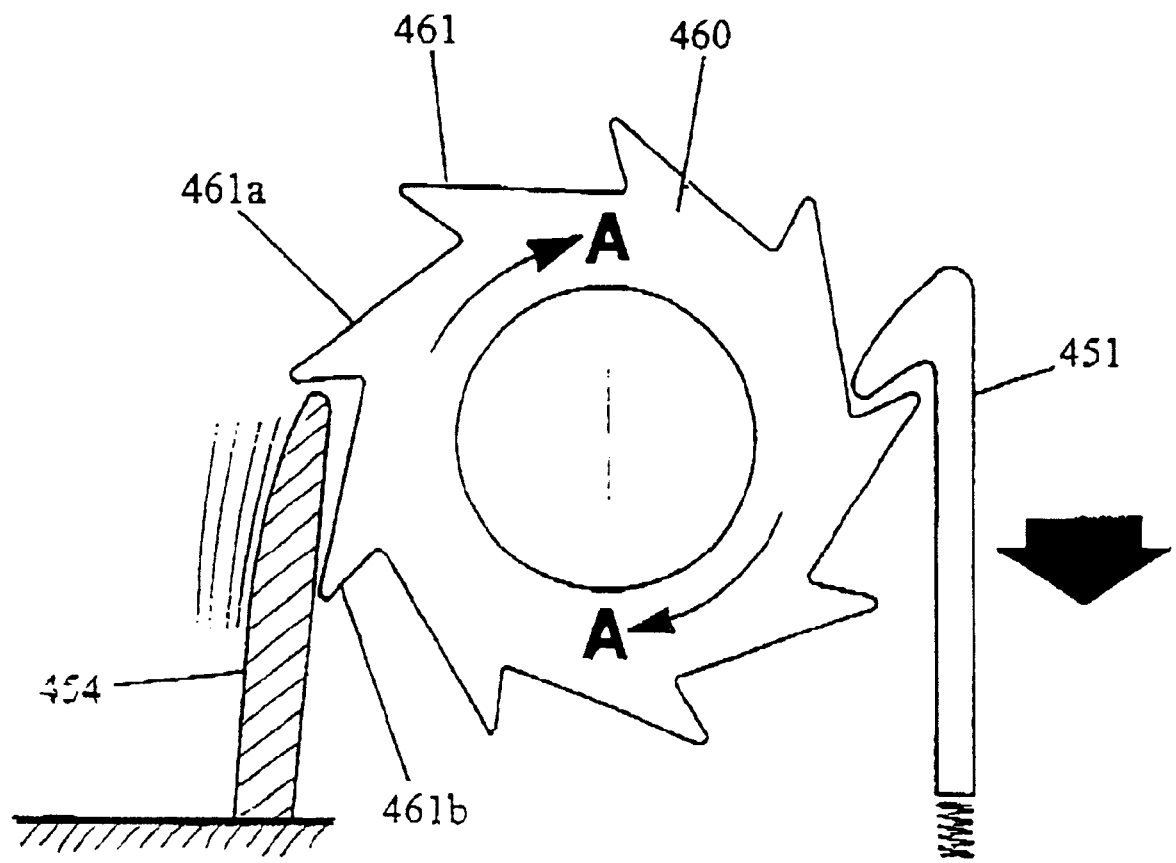
FIG. 4 is a schematic view of a conventional ratchet gear and drive pawl arrangement.

FIG. 4 shows a schematic view of a conventional ratchet gear and drive pawl arrangement which uses a reciprocating drive element 451 acting in a pulling sense to rotate a ratchet-toothed wheel 460 in the direction shown by the arrows A. A fixed pawl 454 acts to prevent reverse rotation of the ratchet-toothed wheel 460 by engagement against the trailing slope 461b of a ratchet tooth 461. However, on forward rotation of the ratchet-toothed wheel 460 in the sense of arrows A, the fixed pawl 454 is capable of radially outward deformation, urged by the leading slope 461a of a ratchet-tooth 461.

In this arrangement, if the ratchet-toothed wheel 460 is rotated by more than a single tooth pitch but by less than two tooth pitches for each reciprocating movement of the drive pawl 451, there is a degree of reverse rotation until the fixed pawl 454 becomes engaged by the trailing slope 461b of a ratchet tooth 461. Thus, the rotation of the ratchet-toothed wheel 460 may be said to be "stepped".

Turning now to FIG. 5 this shows schematically two possible arrangements of ratchet gear and drive pawl in accordance with a first aspect of the invention.

View (a) shows a drive pawl hook element 551 acting in the sense of arrow B to pull the ratchet teeth 561 of a ratchet-toothed wheel 560 downwards and effect clockwise rotation of the ratchet-toothed wheel 560. The control surface 571 guides the top of the drive pawl hook element 551 and delimits the position at which the drive pawl hook element 551 makes first contact with a ratchet-tooth 561 during its downward motion. Equally, the control surface 571 forces the drive pawl hook element 551 to disengage from the ratchet tooth 561 at a fixed point during its downward path.

View (b) shows a similar arrangement in which a drive pawl 550 acts in a pushing sense in the direction of arrow B to rotate the ratchet-toothed wheel 560 in a clockwise sense. Again, the natural tendency of the drive pawl tip 551 to follow a ratchet tooth 561 around its curved path is prevented by the control surface 571.

FIG. 6(a) shows a similar arrangement to the conventional ratchet gear and drive pawl mechanism depicted in FIG. 4 and described above. In this particular arrangement, however, the drive pawl 650 is acting in a pushing sense in the direction of arrow B to drive the ratchet-toothed wheel 660 clockwise. Fixed pawl 654 acts to prevent reverse rotation of the ratchet-toothed wheel 660, but its action is not continuous and the restraint is said to be "stepped".

View 6(b) shows a similar arrangement in which the fixed pawl 654 is replaced by a coil spring 664 which acts on a spindle rotatably supporting the ratchet-toothed wheel 660. The coils of the spring 664 are oriented such that forward actuation of the drive pawl 650 in the sense of arrow B acts to unwind the coiling slightly, allowing free rotation of the spindle, and hence the ratchet-toothed wheel 660, in the clockwise sense. Reverse rotation of the spindle acts to tighten the coiling of the spring 664 slightly so that it grips the spindle and restrains it against reverse rotation. In this sense, the restraint is "stepless".

Referring now to FIG. 7, here is a series of schematic views showing two arrangements of a conventional ratchet drive and two arrangements of a straddle drive in accordance with a third aspect of the invention.

View (a) shows a conventional pushing arrangement where a drive pawl 751 actuated in the direction of arrow B engages a ratchet tooth 761 of ratchet-toothed wheel 760 to rotate it in a clockwise sense. In order to achieve effective engagement between the tip of the drive pawl 751 and the valley in between neighbouring ratchet teeth 761, the tip of the drive pawl 751 must be quite slender. This means that it is susceptible to bending and, whilst the bending moment aids engagement of the drive pawl tip with the ratchet teeth 761, the bending moment reduces the effective travel. In a counter, this could affect counting precision.

View (b) shows a ratchet-toothed wheel 760 rotated in a clockwise sense by a straddle form of drive pawl 751 actuated in the pushing sense represented by arrow B. The ratchet tooth-engaging element is supported at both ends by a support arm 752, 753. In this arrangement, the ratchet tooth-engaging element is acting in pure compression. Moreover, the support arms 752, 753 can be made sufficiently sturdy to withstand bending because they do not need to come into contact with the ratchet-toothed wheel 760.

View (c) is similar to the arrangement shown in view (a) but relates to the case in which the drive pawl 751 acts in the pulling sense. In this arrangement, the tip of the drive pawl 751 is fashioned in the form of a hook engageable behind the trailing slopes 761b of the ratchet teeth 761 to pull the ratchet-toothed wheel 760 around in the clockwise direction. The hook must of necessity be fairly slender in order to achieve effective engagement with the ratchet teeth 761. However, this means that the tip of the drive pawl 751 is susceptible to bending. In this case, the tendency is for radially outward bending, encouraging premature disengagement of the drive pawl 751 from the ratchet-toothed wheel 760. Again, this leads to a shortening of the effective stroke and may undermine count precision in a counter apparatus.

View (d) shows a straddle form of drive pawl 751 acting in the pulling sense. The ratchet tooth-engaging element is supported at both ends by a support arm 752, 753. In this embodiment, the ratchet tooth-engaging element acts in pure compression. Furthermore, support arms 752, 753 may be sufficiently thick to withstand bending because they straddle the ratchet-toothed wheel 760 and do not need to come into contact with it.

A further benefit of this arrangement, in both its push and pull forms, is that by supporting the tooth-engaging element at both its ends, it can be reduced in profile to a knife edge for maximum precision of engagement with the ratchet teeth 761.

Although the invention has been particularly described above with reference to specific embodiments, it will be understood by persons skilled in the art that these are merely illustrative and that variations are possible without departing from the scope of the claims which follow.

What is claimed is:

1. A dose counter for a metered dose inhaler, the counter comprising:

actuator means;

rotary gear means having a wheel mounted on a spindle, said wheel having a plurality of ratchet teeth around a periphery of said wheel;

drive means for driving said rotary gear means in stepwise fashion in response to displacement of said actuator means;

reverse rotation prevention means to prevent reverse rotation of said rotary gear means;

display means coupled to said rotary gear means, said display means having a visible array of incrementing integers on a surface thereof indexable by a single integer in response to each step of the step-wise motion of the rotary gear means; and a control surface to regulate a position of engagement and disengagement between said drive means and said wheel, wherein the reverse rotation prevention means is a friction clutch.

2. A dose counter as claimed in claim 1 wherein the friction clutch is a wrap-spring clutch.

3. A dose counter as claimed in claim 1 wherein the drive means comprises a ratchet drive pawl in the form of a straddle drive in which an engagement element that engages the ratchet teeth of the wheel is supported between a pair of spaced apart support arms.

4. A dose counter as claimed in claim 1 wherein the display means is an elongate flexible web on which a dose count is printed or written.

5. A dose counter for a metered dose inhaler, the counter comprising:

actuator means;

rotary gear means having a wheel mounted on a spindle, said wheel having a plurality of ratchet teeth around a periphery of said wheel;

drive means for driving said rotary gear means in step-wise fashion in response to displacement of said actuator means;

display means coupled to said rotary gear means, said display means having a visible array of incrementing integers on a surface thereof indexable by a single integer in response to each step of the step-wise motion of the rotary gear means; and stepless restraint means to prevent reverse rotation of said rotary gear means, wherein the stepless restraint means is a wrap-spring clutch operating on the spindle on which the wheel is mounted and bracing the spindle against reverse rotation.

6. A dose counter as claimed in claim 5 wherein the actuator means are operable by linear displacement from a first position to a second position and back to said first position and wherein a count index occurs either during a forward stroke of the actuator means from said first position to said second position or during a return stroke of the actuator means from said second position to said first position.

7. A dose counter as claimed in claim 6 wherein the actuator means comprise a spring-loaded plunger adapted to engage a rim of a medicament reservoir, said plunger being depressible against the return force of the spring loading when the medicament reservoir is translated to deliver a dose of medicament through a metering valve.

8. A dose counter as claimed in claim 5 wherein the drive means comprises a ratchet drive pawl in the form of a straddle drive in which an engagement element that engages the ratchet teeth of the wheel is supported between a pair of spaced apart support arms.

9. A dose counter as claimed in claim 5 wherein the display means is an elongate flexible web on which a dose count is printed or written.

10. A dose counter for a metered dose inhaler, the counter comprising:

actuator means;

rotary gear means having a wheel mounted on a spindle, said wheel having a plurality of ratchet teeth around a periphery of said wheel;

drive means for driving rotary gear means in step-wise fashion in response to displacement of said actuator means;

display means coupled to, said display means having a visible array of incrementing integers on a surface thereof indexable by a single integer in response to each step of the step-wise motion of the rotary gear means; and a ratchet and drive pawl mechanism including a rack having an array of ratchet teeth and drive pawl means in the form of a straddle drive in which an element that engages the ratchet teeth of the rack is supported between a pair of spaced apart support arms.

11. A dose counter as claimed in claim 10 wherein a gap between the support arms is dimensioned to accommodate a thickness of the rack therebetween.

12. A dose counter for a metered dose inhaler, the counter comprising:

actuator means;

rotary gear means having a wheel mounted on a spindle, said wheel having a plurality of ratchet teeth around a periphery of said wheel;

drive means for driving said rotary means in step-wise fashion in response to displacement of said actuator means;

reverse rotation prevention means to prevent reverse rotation of said rotary gear means;

display means coupled to said rotary gear means, said display means having a visible array of incrementing integers on a surface thereof indexable by a single integer in response to each step of the step-wise motion of the rotary gear means; and a control surface to regulate a position of engagement and disengagement between said drive means and said wheel, wherein the drive means comprises a ratchet drive pawl in the form of a straddle drive in which an engagement element that engages the ratchet teeth of the wheel is supported between a pair of spaced apart support arms.

13. A dose counter as claimed in claim 12 wherein the actuator means are operable by linear displacement from a first position to a second position and back to said first position and wherein a count index occurs either during a forward stroke of the actuator means from said first position to said second position or during a return stroke of the actuator means from said second position to said first position.

14. A dose counter as claimed in claim 13 wherein the actuator means comprises a spring-loaded plunger adapted to engage a rim of a medicament reservoir, said plunger being depressible against the return force of the spring loading when the medicament reservoir is translated to deliver a dose of medicament through a metering valve.

15. A dose counter as claimed in claim 12 wherein the reverse rotation prevention means is a friction clutch.

16. A dose counter as claimed in claim 15 wherein the friction clutch is a wrap-spring clutch.

17. A dose counter as claimed in claim 12 wherein the display means is an elongate flexible web on which a dose count is printed or written.

18. A dose counter for a metered dose inhaler, the counter comprising:

actuator means;

rotary gear means having a wheel mounted on a spindle, said wheel having a plurality of ratchet teeth around a periphery of said wheel;

drive means for driving said rotary gear means in step-wise fashion in response to displacement of said actuator means;

reverse rotation prevention means to prevent reverse rotation of said rotary gear means;

display means coupled to said rotary gear means, said display means having a visible array of incrementing integers on a surface thereof indexable by a single integer in response to each step of the step-wise motion of the rotary gear means; and a control surface to regulate a position of engagement and disengagement between said drive means and said wheel, wherein the display means is an elongate flexible web on which a dose count is printed or written.

19. A dose counter as claimed in claim 18 wherein the actuator means are operable by linear displacement from a first position to a second position and back to said first position and wherein a count index occurs either during a forward stroke of the actuator means from said first position to said second position or during a return stroke of the actuator means from said second position to said first position.

20. A dose counter as claimed in claim 19 wherein the actuator means comprises a spring-loaded plunger adapted to engage a rim of a medicament reservoir, said plunger being depressible against the return force of the spring loading when the medicament reservoir is translated to deliver a dose of medicament through a metering valve.

21. A dose counter as claimed in claim 18 wherein the reverse rotation prevention means is a friction clutch.

22. A dose counter as claimed in claim 21 wherein the friction clutch is a wrap-spring clutch.

23. A dose counter as claimed in claim 18 wherein the drive means comprises a ratchet drive pawl in the form of a straddle drive in which an engagement element that engages the ratchet teeth of the wheel is supported between a pair of spaced apart support arms.

24. A dose counter for a metered dose inhaler, the counter comprising:

actuator means;

rotary gear means having a wheel mounted on a spindle, said wheel having a plurality of ratchet teeth around a periphery of a wheel;

drive means for driving said rotary gear means in step-wise fashion in response to displacement of said actuator means;

display means coupled to, said display means having a visible array of incrementing integers on a surface thereof indexable by a single integer in response to each step of the step-wise motion of the rotary gear means; and stepless restraint means to prevent reverse rotation of said rotary gear means, wherein the drive means comprises a ratchet drive pawl in the form of a straddle drive in which an engagement element that engages the ratchet teeth of the wheel is supported between a pair of spaced apart support arms.

25. A dose counter as claimed in claim 24 wherein the stepless restraint means is a wrap-spring clutch operating on the spindle on which the wheel is mounted and bracing the spindle against reverse rotation.

26. A dose counter as claimed in claim 25 wherein the actuator means comprise a spring-loaded plunger adapted to engage a rim of a medicament reservoir, said plunger being depressible against the return force of the spring loading when the medicament reservoir is translated to deliver a dose of medicament through a metering valve.

27. A dose counter as claimed in claim 24 wherein the actuator means are operable by linear displacement from a first position to a second position and back to said first position and wherein a count index occurs either during a forward stroke of the actuator means from said first position to said second position or during a return stroke of the actuator means from said second position to said first position.

28. A dose counter as claimed in claim 24 wherein the display means is an elongate flexible web on which a dose count is printed or written.

29. A dose counter for a metered dose inhaler, the counter comprising:

actuator means;

rotary gear means having a wheel mounted on a spindle, said wheel having a plurality of ratchet teeth around a periphery of a wheel;

drive means for driving said rotary gear means in step-wise fashion in response to displacement of said actuator means;

display means coupled to said rotary gear means, said display means having a visible array of incrementing integers on a surface thereof indexable by a single integer in response to each step of the step-wise motion of the rotary gear means; and stepless restraint means to prevent reverse rotation of said rotary gear means, wherein the display means is an elongate flexible web on which a dose count is printed or written.

30. A dose counter as claimed in claim 29 wherein the stepless restraint means is a wrap-spring clutch operating on the spindle on which the wheel is mounted and bracing the spindle against reverse rotation.

31. A dose counter as claimed in claim 29 wherein the actuator means are operable by linear displacement from a first position to a second position and back to said first position and wherein a count index occurs either during a forward stroke of the actuator means from said first position to said second position or during a return stroke of the actuator means from said second position to said first position.

32. A dose counter as claimed in claim 31 wherein the actuator means comprise a spring-loaded plunger adapted to engage a rim of a medicament reservoir, said plunger being depressible against the return force of the spring loading when the medicament reservoir is translated to deliver a dose of medicament through a metering valve.

33. A dose counter as claimed in claim 29 wherein the drive means comprises a ratchet drive pawl in the form of a straddle drive in which an engagement element that engages the ratchet teeth of the wheel is supported between a pair of spaced apart support arms.

* * * * *